(12) United States Patent
Son et al.

(10) Patent No.: US 8,710,105 B2
(45) Date of Patent: Apr. 29, 2014

(54) METHOD OF PREPARING ENTERIC HARD CAPSULE AND ENTERIC HARD CAPSULE PREPARED THEREBY

(75) Inventors: Jin Ryul Son, Incheon (KR); Hyon Ho Baek, Incheon (KR); Eun Hee Park, Incheon (KR); Sung Wan Lee, Incheon (KR); Min Gyu Song, Seoul (KR); Ja Hyun Cha, Incheon (KR); Jae Uk Cha, Seoul (KR); Won Hwa Ko, Incheon (KR)

(73) Assignee: Samsung Fine Chemicals Co., Ltd. (KR)

( * ) Notice: Subject to any disclaimer, the term of this patent is extended or adjusted under 35 U.S.C. 154(b) by 51 days.

(21) Appl. No.: 13/634,590

(22) PCT Filed: Feb. 21, 2011

(86) PCT No.: PCT/KR2011/001118
§ 371 (c)(1),
(2), (4) Date: Sep. 13, 2012

(87) PCT Pub. No.: WO2011/155686
PCT Pub. Date: Dec. 15, 2011

(65) Prior Publication Data
US 2013/0072579 A1    Mar. 21, 2013

(30) Foreign Application Priority Data

Jun. 11, 2010   (KR) .......................... 10-2010-0055470

(51) Int. Cl.
*A61K 47/38*   (2006.01)
(52) U.S. Cl.
USPC ......................................... 514/781; 424/451

(58) Field of Classification Search
None
See application file for complete search history.

(56) References Cited

U.S. PATENT DOCUMENTS 4,138,013 A    2/1979   Okajima

FOREIGN PATENT DOCUMENTS

JP    2006-016372 A    1/2006

OTHER PUBLICATIONS

Written Opinion for International Application No. PCT/KR2011/001118 dated Nov. 24, 2011.
International Search Report for International Application No. PCT/KR2011/001118 dated Nov. 24, 2011.

*Primary Examiner* — David J Blanchard
*Assistant Examiner* — Daniel F Coughlin
(74) *Attorney, Agent, or Firm* — Cantor Colburn LLP

(57) ABSTRACT

A method of preparing enteric hard capsules, and an enteric hard capsule prepared by the method. The method may include: dissolving an enteric base material, a capsule forming aid, and a neutralizing agent in water at room temperature to prepare an aqueous composition; heating the aqueous composition to a first temperature that is higher than a gelation start temperature of the aqueous composition; cooling the heated aqueous composition to a second temperature that is lower than the gelation start temperature; immersing a mold pin heated to a third temperature that is higher than the gelation start temperature into the aqueous composition; removing the mold pin from the aqueous composition to obtain a film coated on the mold pin; maintaining the film on the mold pin at a fourth temperature that is higher than the gelation start temperature for a first time period to fix the film onto the mold pin; and drying the fixed film at a fifth temperature for a second time period to obtain a capsule shell.

6 Claims, 2 Drawing Sheets

METHOD OF PREPARING ENTERIC HARD CAPSULE AND ENTERIC HARD CAPSULE PREPARED THEREBY

TECHNICAL FIELD

This application claims the benefit of Korean Patent Application No. 10-2010-0055470, filed on Jun. 11, 2010, in the Korean Intellectual Property Office, the disclosure of which is incorporated herein in its entirety by reference.

The present invention relates to a method of preparing an enteric hard capsule, and an enteric hard capsule prepared by the method. More particularly, the present invention relates to a method of preparing an enteric hard capsule in which an aqueous composition that contains an enteric base material, a capsule forming aid, and a neutralizing agent is used to prepare the enteric hard capsule, and an enteric hard capsule prepared by the method.

BACKGROUND ART

Capsules for pharmaceutical preparations and neutraceutical preparations are generally prepared using gelatin and hydroxypropyl methylcellulose (HPMC) as base materials.

Gelatin capsules have high industrial productivity and high price competitiveness. However, if gelatin capsules contain 10 wt % moisture or less, they may lose plasticity and may show serious deterioration in impact resistance. Concern on mad cow diseases has limited the use of gelatin capsules. For these reasons, plant-based HPMC capsules prepared without gelatin have drawn attention.

According to gelation properties, hard capsule preparation methods may be roughly classified into two methods: cold gelation and thermal gelation.

First, cold gelation involves: heating a solution including a gelatin that may gelate at room temperature, or an HPMC solution containing carrageenan, agar, sodium alginate, gellan gum, and/or pectin that may gelate at room temperature; maintaining the solution at a high temperature to age it; immersing a cold mold pin in the solution so that the mold pin is coated with a predetermined amount of the solution; and removing the mold pin from the solution, immediately applying cold air at a temperature of about 20° C. to the solution on the mold pin to gelate the gelatin or HPMC of the solution, and drying the gel. Gelating agents such as carrageenan, sodium alginate, gellan gum, pectin, or the like are widely used in cold gelation to form capsules because they have increased gelation capability due to bonding to metal ions, such as potassium, calcium, and sodium. However, when a capsule including foreign substances, such as carrageenan, is orally administered, the foreign substances may react with metal salts in gastric juice or intestinal juice, so that a binding force among components of the capsule may be increased, thereby inhibiting the capsule from disintegrating.

Next, thermal gelation is based on the gellation characteristics of HPMC in a solution when heated at high temperatures. A high-temperature mold pin is immersed in an HPMC solution maintained at a temperature higher than or equal to room temperature so as to be coated with the HPMC solution, and HPMC of the HPMC solution coated on the mold pin is gelated by the heat of the mold pin, thereby preparing hard capsules.

However, if the capsules are disintegrated by gastric juice, they may not be used as capsules for pharmaceutical or neutraceutical preparations when the main ingredients and excipients of the preparations filled in the capsule are unstable to acid, or may cause stomach irritation or an odor generated therefrom to regurgitate. To solve the above problems, the surfaces of the capsules containing ingredients may be coated with an enteric base material to give enteric properties.

However, the method of coating capsules with an enteric base material may require an additional coating process and increase production costs. Furthermore, an organic solvent in a coating solution is highly likely to remain on the capsule surface after the coating, capsule identification codes on the surfaces may not be visible due to the coating, or the capsules may have poor appearance, as compared to before the coating.

To address these drawbacks, many researchers have been tried to develop various kinds of enteric capsules. However, enteric hard capsules with high quality and high industrial productivity have not yet been commercialized.

DISCLOSURE OF INVENTION

Technical Problem

The present invention provides a method of preparing an enteric hard capsule using an aqueous composition that includes an enteric base material, a capsule forming aid, and a neutralizing agent.

The present invention provides an enteric hard capsule prepared by the method.

Solution to Problem

According to an aspect of the present invention, there is provided a method of preparing an enteric hard capsule, the method including: dissolving an enteric base material, a capsule forming aid, and a neutralizing agent in water at room temperature to prepare an aqueous composition; heating the aqueous composition to a first temperature that is higher than a gelation start temperature of the aqueous composition; cooling the heated aqueous composition to a second temperature that is lower than the gelation start temperature; immersing a mold pin heated to a third temperature that is higher than the gelation start temperature into the aqueous composition; removing the mold pin from the aqueous composition to obtain a film coated on the mold pin; maintaining the film on the mold pin at a fourth temperature that is higher than the gelation start temperature for a first time period to fix the film onto the mold pin; and drying the fixed film at a fifth temperature for a second time period to obtain a capsule shell.

The first temperature may be higher than the gelation start temperature by about 1° C. to about 20° C.

The second temperature may be lower than the gelation start temperature by about 15° C. to about 40° C.

The third temperature may be higher than the gelation start temperature by about 10° C. to about 40° C.

The fourth temperature may be from about 60° C. to about 80° C., and the first time period may be from about 1 minute to about 15 minutes.

The fifth temperature may be from about 20° C. to about 40° C., and the second time period may be from about 30 minutes to about 60 minutes.

The enteric base material may include at least one compound selected from the group consisting of hydroxypropyl methyl cellulose phthalate (HPMCP) and hydroxypropyl methyl cellulose acetate succinate (HPMCAS).

The capsule forming aid may include cellulose ether.

The cellulose ether may include at least one compound selected from the group consisting of hydroxypropyl methylcellulose (HPMC) and methylcellulose (MC).

The neutralizing agent may include an alkaline material.

An amount of the enteric base material may be from about 8% to about 25% based on the total weight of the aqueous composition.

An amount of the capsule forming aid may be from about 1% to about 12% based on the total weight of the aqueous composition.

An amount of the neutralizing agent may be from about 0.5% to about 5% based on the total weight of the aqueous composition.

The aqueous composition may further include about 0.01% to about 1.0% of an emulsifier based on the total weight of the aqueous composition.

The aqueous composition may further include about 0.1% to about 4.0% of a plasticizer based on the total weight of the aqueous composition.

According to an aspect of the present invention, there is provided an enteric hard capsule prepared by any of the methods described above.

Advantageous Effects of Invention

According to the one or more embodiments of the present invention, high-quality enteric hard capsules may be prepared from an aqueous composition containing an enteric base material, a capsule forming aid, and a neutralizing agent. Enteric hard capsules prepared from the aqueous composition by a method according to the one or more embodiments of the present invention may have similar standard characteristics and functions to those prepared by conventional methods, and may not disintegrate or dissolve in gastric juice conditions (at a pH of about 1.2) for 2 to 4 hours, but may disintegrate and dissolve in the small intestinal juice condition (at a pH of about 6.8) within a short time period of 10 minutes. Enteric hard capsules according to the one or more embodiments of the present invention may be prepared using conventional equipment. The aqueous composition according to the one or more embodiments of the present invention may have physical characteristics and processing conditions that are readily applicable in commercial production on a large scale.

BRIEF DESCRIPTION OF DRAWINGS

The above and other features and advantages of the present invention will become more apparent by describing in detail exemplary embodiments thereof with reference to the attached drawings in which.

MODE FOR THE INVENTION

Figure 1:
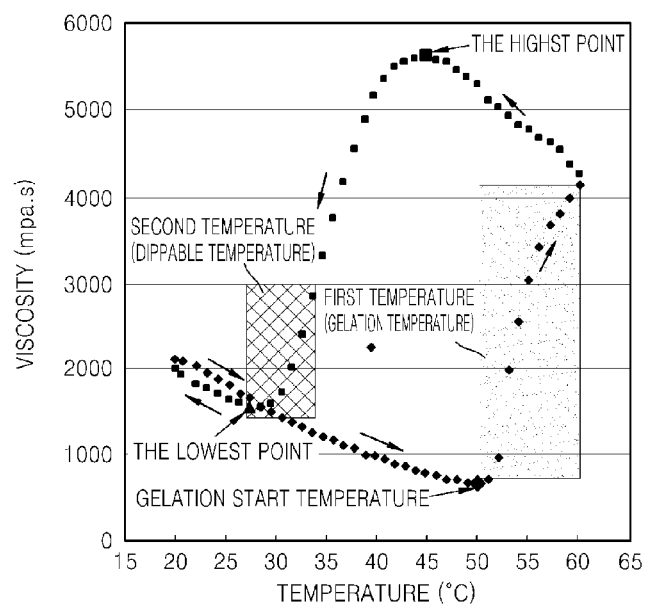
FIG. 1 is a graph illustrating the relationship between temperatures and viscosities of an aqueous composition at different preparation steps in a method of preparing enteric hard capsules according to an embodiment of the present invention.

According to the current embodiment, the method of preparing an enteric hard capsule may include the following steps.

A first step is to prepare an aqueous composition by adding an enteric base material, a capsule forming aid, a neutralizing agent, and the like to water at room temperature (for example, at a temperature of about 20° C. to about 30° C.). As used herein, the term "aqueous composition" indicates a composition in which at least one of an enteric base material, a capsule forming aid, and a neutralizing agent are at least partially dissolved in water and/or at least partially gelled.

The enteric base material is not disintegrated at a pH of the gastric juice (pH of about 1.2) for at least about 2 to 4 hours, but is rapidly disintegrated at a pH of the small intestinal juice (pH of about 6.8) within 10 minutes. The enteric base material may include at least one compound selected from the group consisting of hydroxypropyl methyl cellulose phthalate (HPMCP) and hydroxypropyl methyl cellulose acetate succinate (HPMCAS). Examples of the HPMCP include HPMCP HP-55 (containing 18-22 wt % of methoxy group, 5-9 wt % of hydroxypropoxy group, and 27-35 wt % of phthalyl group; 200731 Type; and a viscosity of 32 to 48 cSt (centistokes)), HPMCP HP-55S (containing 18-22 wt % of methoxy, 5-9 wt % of hydroxypropoxy, and 27-35 wt % of phthalyl group; 200731 Type; and a viscosity of 136 to 204 cSt), and HPMCP HP-50 (containing 20-24 wt % of methoxy, 6-10 wt % of hydroxypropoxy, and 21-27 wt % of phthalyl group; 220824 Type; and a viscosity of 44 to 66 cSt), which are produced by Samsung Fine Chemicals Co., Ltd. Throughout the specification, the term "viscosity" indicates the viscosity measured using an Anton-Paar MCR 301 (heating rate: 2° C./min, Spindle No.: CC 27 8009, RPM (shear rate): 1/s; available from Anton Paar), and specifically the term "viscosity of the HPMCP" indicates the viscosity of 20 wt % aqueous solution of the HPMCP measured as described above. The amounts of the methoxy group, hydroxypropoxy group and phthalyl group in weight percentage are based on the total weight of each of the HPMCP and HPMCAS, respectively. The amount of the enteric base material may be from about 8% to about 25% based on the total weight of the aqueous composition, and in some embodiments, may be from about 12% to about 21%. In this regard, the aqueous composition may have a viscosity of about 1000 cps (centipoises) to about 3000 cps at room temperature. When the amount of the enteric base material is within these ranges, the aqueous composition may have a viscosity that is appropriate to form a capsule film with an appropriate thickness, and capsules formed from the aqueous composition may have good enteric characteristics.

The capsule forming aid may improve elasticity of the fragile enteric capsule film and capsule formability, and may enable to adjust the gelation start temperature of the aqueous composition to a temperature range of, for example, about 20° C. to about 70° C., applicable in commercial production. The capsule forming aid may include cellulose ether. As used herein, the term "gelation start temperature" indicates the temperature at which the viscosity of the aqueous composition that has declined with increasing temperatures during the viscosity measurement performed while heating begins to increase. The cellulose ether may include at least one compound selected from the group consisting of hydroxypropyl methylcellulose (HPMC) and methylcellulose (MC). The HPMC may include about 4 wt % to about 12 wt %, for example, about 4 wt % to about 7.5 wt %, of hydroxypropoxy group, and about 19 to about 30 wt %, for example, about 27 wt % to about 30 wt %, of methoxy group. The amounts of the hydroxypropoxy group and methoxy group in weight percentage are based on the total weight of the HPMC. The viscosity of 2 wt % aqueous solution of the HPMC may be from about 3 cps to about 50 cps, for example, from about 3 cps to about 15 cps. The amount of the capsule forming aid may be from about 1 wt % to about 12%, for example, from about 3 wt % to about 10 wt %, based on the total weight of the aqueous composition. When the amount of the capsule forming aid is within these ranges, the capsule formability may be good, and the resulting capsules may have good elasticity and good enteric characteristics.

The neutralizing agent may solubilize the enteric base material, and may be an alkaline material such as sodium hydroxide, aqueous ammonia, potassium hydroxide, and calcium hydroxide. The neutralizing agent may affect the gelation start temperature. The amount of the neutralizing agent may be from about 0.5 wt % to about 5 wt %, for example, about 1 wt % to about 2.5 wt %, based on the total weight of the aqueous composition. When the amount of the neutralizing agent is within these ranges, the enteric base material may be easily solublized, the aqueous composition may have an appropriate pH, and the resulting capsules may have good enteric characteristics.

The aqueous composition may further include an emulsifier to improve capsule formability. Examples of the emulsifier include sodium lauryl sulfate (SLS), sugar ester (SE), and a mixture thereof. In particular, the SLS may greatly improve the capsule formability. The amount of the emulsifier may be from about 0.01 wt % to about 1.0 wt %, for example, from about 0.05 wt % to about 0.5 wt %, based on the total weight of the aqueous composition. When the amount of the emulsifier is within these ranges, the aqueous composition may be less likely to roll up when being coated on a mold pin, and thus may have good film formability. The resulting capsules also may have good quality and good safety in regards to gastroenteric disorders when dosed.

The aqueous composition may further include a plasticizer to improve a film strength of the capsule. The plasticizer may include at least one compound selected from the group consisting of glycerin, hydrogenated corn syrup, triethyl citrate (TEC), triacetin (TA), polyethylene glycol (PEG), and propylene glycol (PG). The amount of the plasticizer may be from about 0.1 wt % to about 4.0 wt %, for example, from about 0.2 wt % to about 2.0 wt %, based on the total weight of the aqueous composition. When the amount of the plasticizer is within these ranges, the capsule film may have appropriate plasticity and good transparency and strength.

The aqueous composition prepared as described above may have a pH of from about 4.5 to about 6.5, and a viscosity of from about 1000 cps to about 3000 cps, for example, from about 1500 cps to about 2500 cps, at room temperature. The gelation start temperature of the aqueous composition may vary depending on the mixing ratio of the enteric base material, the capsule forming aid, and the neutralizing agent. For example, the gelation start temperature of the aqueous composition may be adjusted to be from about 40° C. to about 60° C.

The aqueous composition may further include at least one of titanium dioxide and other colorants, such as a mineral pigment, a natural pigment, or a tar pigment.

A second step is to heat the aqueous composition to a first temperature (i.e., a gelation temperature) that is higher than the gelation start temperature thereof.

A third step is to cool the heated aqueous composition to a second temperature (i.e., an immersion temperature) that is lower than the gelation start temperature of the aqueous composition.

A fourth step is to immerse a mold pin heated to a third temperature that is higher than the gelation start temperature into the aqueous composition.

A fifth step is to remove the mold pin from the aqueous composition to obtain a film coated on the mold pin.

A sixth step is to maintain the film at a fourth temperature that is higher than the gelation start temperature for a first time period to fix the film onto the mold pin.

A seventh step is to dry the fixed film at a fifth temperature for a second time period to obtain a capsule shell.

Specifically, the above-described method of preparing enteric hard capsules is characterized by the following four main factors.

The first factor is the gelation temperature (i.e., the first temperature). The gelation temperature of the aqueous composition of the present application is higher than the gelation start temperature thereof. In particular, the aqueous composition prepared at room temperature is at least partially gelated by being heated to the gelation temperature. The gelation of the aqueous composition may greatly influence the flowability of the aqueous composition on the mold pin and may stabilize film formability. The gelation temperature of the aqueous composition may be higher than the gelation start temperature thereof by about 1° C. to about 20° C., for example, by about 5° C. to about 10° C. When the gelation temperature (the first temperature) of the aqueous composition is within these ranges, a capsule film having an appropriate thickness may be obtained within a relatively short period of time without consumption of excess heat energy.

The second factor is the immersion temperature (i.e., the second temperature). As used herein, the term "immersion temperature" indicates the temperature of the aqueous composition which may form uniform capsule film having an appropriate thickness (for example, about 0.1 mm to about 0.15 mm) on the mold pin immersed thereinto. The immersion temperature of the aqueous composition may be lower than the gelation start temperature thereof by about 15° C. to about 40° C., for example, by about 20° C. to about 35° C. When the immersion temperature (the second temperature) is within these ranges, a uniform capsule film having an appropriate thickness may be obtained. In particular, when a mold pin is immersed in the aqueous composition that has reached the immersion temperature, the mold pin may have a uniform capsule film thereon having an appropriate thickness. This is attributed to that the aqueous composition has an appropriate viscosity at the immersion temperature. The viscosity of the aqueous composition may be appropriately adjusted by adding water to the aqueous composition while the immersion temperature is maintained, thereby appropriately adjusting the thickness of the capsule film. While being cooled from the first temperature to the second temperature, a viscosity of the aqueous composition may reach a maximum value near the gelation temperature, and the viscosity may decrease more sharply nearer the second temperature. In FIG. 1, the maximum viscosity and the temperature of the aqueous composition at the maximum viscosity are denoted as "the highest point". Referring to FIG. 1, a point on the graph corresponding to a minimum viscosity the aqueous composition may have when cooled from the highest point, and the temperature of the aqueous composition at the minimum viscosity are denoted as "the lowest point". As used herein, the term "immersion temperature" indicates a temperature range in which the aqueous composition may have a viscosity of from about 3000 mpa·s or less to a viscosity at the lowest point.

The third factor is the temperature of the mold pin. The temperature of the mold pin pre-heated prior to being immersed into the aqueous composition is an important factor to determine the thickness of the capsule film. The thickness of the capsule film may be adjusted by varying the temperature of the mold pin. That is, the thickness of the capsule film may become thinner with the decreasing temperature of the mold pin, and vice versa. The temperature of the mold pin depends on the capsule size. However, the temperature of the mold pin may be maintained at a temperature (the third temperature) that is higher than the gelation start temperature of the aqueous composition by about 10° C. to about 40° C. When the third temperature is within this range, a capsule having an appropriate film thickness may be obtained.

The fourth factor is the drying temperature. The drying temperature may control the flowability of the aqueous composition coated on the mold pin. Conventionally, the aqueous composition coated on the mold pin is transferred to a drying device and undergoes a drying process. In the beginning of the drying process, the drying temperature is maintained at a temperature (the fourth temperature) that is higher than or equal to the gelation start temperature for a predetermined time period (the first time period) to completely fix the aqueous composition on the mold pin so that the aqueous composition does not flow down. The fourth temperature may be from about 60° C. to about 80° C. The first time period may be from about 1 minute to about 15 minutes, for example, about 8 minutes. When the fourth temperature and the first time period are within these respective ranges, a capsule without cracks may be obtained. Then, the mold pin with the fixed aqueous composition is left in a drying device at the fifth temperature for the second time period to dry the capsule (i.e. the fixed aqueous composition). The fifth temperature may be from about 20° C. to about 40° C., and the second time period may be from about 30 minutes to about 60 minutes. When the fifth temperature and the second time period are within these respective ranges, a capsule with an excellent strength and without deformations or cracks may be obtained.

By appropriately adjusting these four factors, enteric hard capsules having a similar quality with other commercially available capsules may be prepared. Enteric hard capsules prepared by the method described above may be used in various applications, for example, as capsules for pharmaceutical or neutraceutical preparations and the like.

Hereinafter, one or more embodiments will be described in detail with reference to the examples below. These examples are for illustrative purposes only and are not intended to limit the scope of the invention.

EXAMPLES

Examples 1-2 & Comparative Example 1

Figure 2:
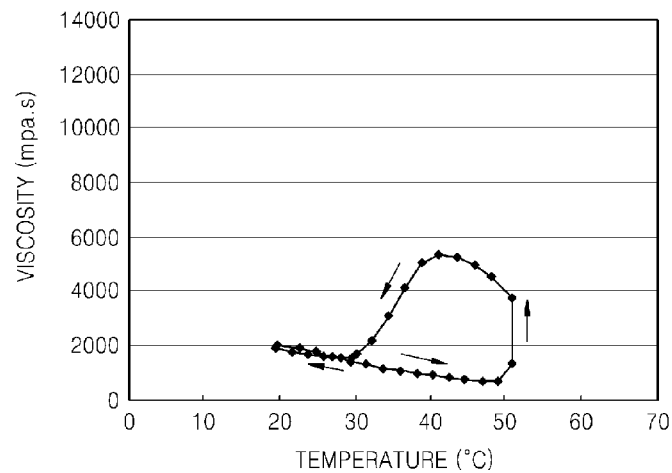
FIG. 2 is a graph illustrating the relationship between temperatures and viscosities of an aqueous composition at different preparation steps in a method of preparing enteric hard capsules according to Example 1.
Figure 3:
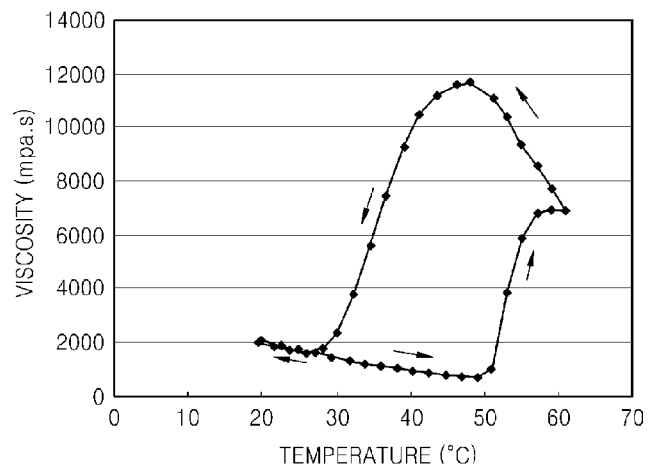
FIG. 3 is a graph illustrating the relationship between temperatures and viscosities of an aqueous composition at different preparation steps in a method of preparing enteric hard capsules according to Example 2.
Figure 4:
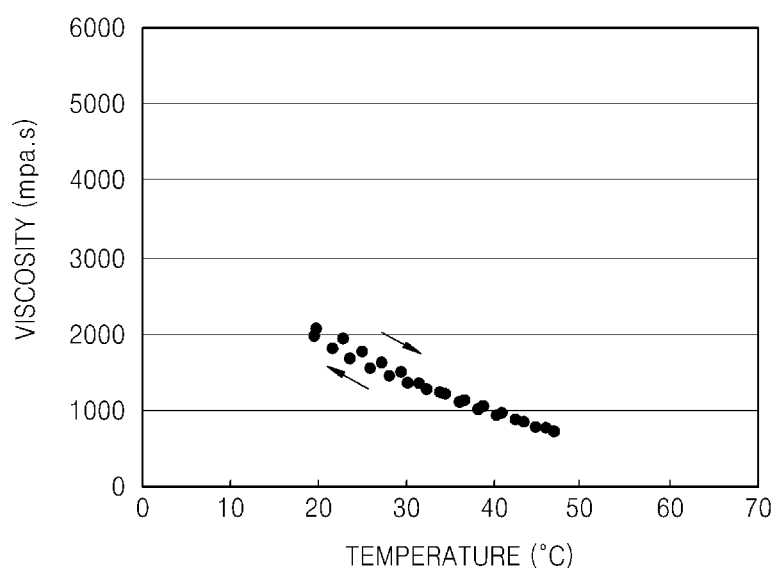
FIG. 4 is graph illustrating the relationship between temperatures and viscosities of an aqueous composition at different preparation steps in a method of preparing enteric hard capsules according to Comparative Example 1.

Preparation of Aqueous Compositions and Certification of Relationship Between Temperature And Viscosity of Each Aqueous Composition 13.77 wt % of HPMCP (HPMCP HP-55, available from Samsung Fine Chemicals Co., Ltd.), 5.7 wt % of HPMC 2906 (AnyCoat-C BN4, available from Samsung Fine Chemicals Co., Ltd.), 1.17 wt % of NaOH, and 79.36 wt % of water were mixed to prepare an aqueous composition. The aqueous composition was maintained at a temperature of 20° C. Then, the aqueous composition was aged at room temperature (The aging temperatures for respective Examples are shown in Table 1 below.) for about 12 hours, and was then heated to a gelation or pre-gelation temperature (different gelation temperatures for Examples 1-2 and pre-gelation temperature for Comparative Example 1, see Table 1 below) that is higher or lower than the gelation start temperature (49° C.) of the aqueous composition. The at least partially gelated or non-gelated aqueous composition was then cooled to a temperature of 20° C. The viscosity of the aqueous composition was measured after each of the steps, and relationships between temperature and viscosity of the respective materials to be formed of Examples 1-2 and Comparative Example 1 are shown in FIGS. 2 to 4. The temperatures and viscosities of the materials to be formed only at the lowest and highest points in FIGS. 2 to 4 are shown in Table 1 below. In FIGS. 2 to 4, arrows indicate the direction of heating the materials to be formed at different temperatures. Viscosity was measured using an Anton-Paar MCR 301 (heating rate: 2° C./min, Spindle No.: CC 27 8009, RPM (shear rate): 1/s; available from Anton Paar).

TABLE 1

| | Aging Temperature (° C.) | Gelation or Pre-gelation Temperature (° C.) | The Lowest Point | | The Highest Point | | Immersion temperature*[2] (° C.) |
|---|---|---|---|---|---|---|---|
| | | | Temperature*[1] (° C.) | Viscosity (mpa·s) | Temperature (° C.) | Viscosity (mpa·s) | |
| Example 1 | 28 | 51 | 28 | 1550 | 41 | 5390 | 28~38 |
| Example 2 | 26 | 60 | 26 | 1580 | 47 | 11700 | 26~33 |
| Comparative Example 1 | 25 | 47 | 25 | 1620 | 25 | 1620 | 25 |

*[1]The temperature of the aqueous composition at the lowest point was the same as the aging temperature.
*[2]The immersion temperature indicates the temperature of the aqueous composition having a viscosity of from about 3000 mpa·s or less to a viscosity at the lowest point.

Referring to FIGS. 2 to 4, in both the materials to be formed of Examples 1 and 2, a closed loop may be drawn through the viscosities at different temperatures. However, almost a straight line may be drawn through the viscosities of the aqueous composition of Comparative Example 1 at different temperatures.

Referring to Table 1, the materials to be formed of Examples 1 and 2 have immersion temperature ranges, while the capsule composition of Comparative Example 1 has only immersion temperature at one point. In Examples 1 and 2, the higher the gelation temperature, the lower the immersion temperature, which indicates that the immersion temperature may be varied by adjusting the gelation temperature.

When capsules are prepared using the aqueous composition according to the conditions of Examples 1 and 2, i.e., by heating the aqueous composition to a temperature higher than the gelation start temperature to at least partially gelate the aqueous composition, cooling the at least partially gelated aqueous composition to the immersion temperature to liquify the at least partially gelated aqueous composition, and immersing a mold pin in the liquefied at least partially gelated aqueous composition, the capsules may have a uniform film having an appropriate thickness, as confirmed by Examples 3 to 14 described below. However, when preparing capsules according to Comparative Example 1, i.e., by heating the aqueous composition to a temperature lower than the gelation start temperature, cooling the aqueous composition to the immersion temperature, and immersing a mold pin in the aqueous composition, the resulting capsule films are not uniform and are too thin to form whole capsules, as confirmed by Comparative Example 2 described as follows.

Examples 3-14 and Comparative Example 2

Aqueous compositions listed in Table 2 below were prepared according to the following method, and enteric capsules were prepared in the conditions listed in Table 3 below. Then, each of the prepared capsules was immersed in a test solution at a pH of 1.2, which is similar to the pH of gastric juice, for about 2 hours at maximum to observe whether each capsule disintegrated or not, and then immersed in a test solution at a pH of 6.8, which is similar to the pH of small intestinal juice, to measure disintegration time.

The results are shown in Table 3 below.

(Preparation of Aqueous Compositions)

A neutralizing agent, an emulsifier, and a plasticizer, and optionally, a colorant were added to water, and an enteric base material and a capsule forming aid were added thereto, dissolved, and then aged at room temperature (aging temperature) for about 12 hours to prepare aqueous compositions listed in Table 2 below.

(Preparation of Enteric Capsules)

Each of the aqueous compositions was heated to a gelation temperature (Examples 3-14) or a pre-gelation temperature (Comparative Example 2). Then, the aqueous composition was cooled to a temperature (aging temperature) lower than the gelation start temperature of the aqueous composition. Then, a mold pin (Technophar Equipment & Service Ltd., pin, #0), preheated to a temperature (mold pin temperature) that is higher than the gelation start temperature of the corresponding aqueous composition, was immersed in the aqueous composition (herein, the aqueous composition) so that the mold pin was coated with the aqueous composition. During this step, the aqueous composition coated on the mold pin was at least partially gelated. Then, the mold pin was removed from the aqueous composition. Subsequently, the mold pin was maintained at a temperature of 70° C. for about 5 minutes and was then dried at a temperature of 30° C. for about 45 minutes.

TABLE 2

| | Composition of aqueous composition (wt %)[1] | | | | | | | | | | | | | |
|---|---|---|---|---|---|---|---|---|---|---|---|---|---|---|
| | Enteric base material | | Capsule forming aid | | | | Neutralizing agent | | | | Emulsifier | Plasticizer | | Colorant |
| | HPM-CP[2] | HPM-CAS[3] | MC[4] | HPMC 2910[5] | HPMC 2208[6] | HPMC 2906[7] | Na—OH | NH$_4$—OH | KOH | Ca—(OH)$_2$ | SLS | TEC | PG | TiO$_2$ |
| Example 3 | 15.71 | — | — | 3.93 | — | — | 1.34 | — | — | — | 0.10 | 0.39 | — | — |
| Example 4 | 13.81 | — | — | 5.92 | — | — | 1.17 | — | — | — | 0.10 | 0.37 | — | — |
| Example 5 | 15.60 | — | — | — | — | 3.90 | — | — | 2.03 | — | 0.10 | 0.39 | — | — |
| Example 6 | 15.71 | — | — | — | — | 3.93 | 1.34 | — | — | — | 0.10 | — | 0.39 | — |
| Example 7 | 15.60 | — | — | — | — | 3.90 | — | 2.03 | — | — | 0.10 | — | 0.39 | — |
| Example 8 | 15.74 | — | — | — | — | 3.94 | 0.94 | — | — | 0.16 | 0.10 | — | 0.39 | — |
| Example 9 | 13.80 | — | — | — | — | 5.91 | 0.83 | — | — | 0.14 | 0.10 | — | 0.39 | — |
| Example 10 | 13.69 | — | — | — | 5.87 | — | 1.16 | — | — | — | 0.10 | — | 0.98 | — |
| Example 11 | 15.68 | — | — | — | 3.92 | — | 1.33 | — | — | — | 0.10 | — | 0.59 | — |
| Example 12 | 9.87 | — | — | — | — | 9.87 | 0.83 | — | — | — | 0.10 | — | — | — |
| Example 13 | 13.69 | — | — | — | — | 5.87 | 1.16 | — | — | — | 0.10 | — | 0.59 | 0.39 |
| Example 14 | 15.71 | — | 3.93 | — | — | — | 1.34 | — | — | — | 0.10 | 0.39 | — | — |
| Example 15 | — | 15.24 | — | — | — | 6.54 | 1.50 | — | — | — | 0.10 | — | — | — |
| Comparative Example 2 | 15.71 | — | — | 3.93 | — | — | 1.34 | — | — | -16 | 0.10 | 0.39 | — | — |

[1]The balance of each aqueous composition in Table 2 was water.
[2]HPMCP HP-55, produced by Samsung Fine Chemicals Co., Ltd.
[3]HPMCAS AS-LF, produced by Shin-Etsu Chemical Co., Ltd.
[4]MC 8 cp, produced by Samsung Fine Chemicals Co., Ltd.
[5]AnyCoat-C AN4, produced by Samsung Fine Chemicals Co., Ltd.
[6]AnyCoat-C CN4, produced by Samsung Fine Chemicals Co., Ltd.
[7]AnyCoat-C BN4, produced by Samsung Fine Chemicals Co., Ltd.

TABLE 3

| | Capsule formation conditions[1] | | | | Capsule performance evaluation | | | | |
|---|---|---|---|---|---|---|---|---|---|
| | | | Gelation | | Capsule characteristics[4] | | | | |
| | Aging Temperature (° C.) | Gelation Start Temperature (° C.) | Temperature[2] or Pre-gelation Temperature[3] (° C.) | Mold Pin Temperature (° C.) | Transparency | Gelation strength while being formed | Film Elasticity | Disintegration time (min) | |
| | | | | | | | | pH 1.2 | pH 6.8 |
| Example 3 | 26.0 | 48.0 | 61.0 | 80 | ○ | ◎ | ○ | >120 | 3.15 |
| Example 4 | 26.0 | 46.0 | 61.0 | 76 | ○ | ◎ | ○ | >120 | 3.25 |
| Example 5 | 30.0 | 50.0 | 60.0 | 86 | ○ | ◎ | ◎ | >120 | 3.45 |
| Example 6 | 28.0 | 50.0 | 60.0 | 85 | ○ | ◎ | ◎ | >120 | 3.05 |
| Example 7 | 26.0 | 63.0 | 80.0 | 85 | ○ | ○ | ◎ | >120 | 4.10 |
| Example 8 | 24.0 | 46.0 | 60.0 | 70 | ◎ | ◎ | ◎ | >120 | 3.22 |
| Example 9 | 30.0 | 50.0 | 60.0 | 72 | ◎ | ◎ | ◎ | >120 | 3.52 |

TABLE 3-continued

| | Capsule formation conditions*1 | | | | Capsule performance evaluation | | | | |
|---|---|---|---|---|---|---|---|---|---|
| | | Gelation | | | Capsule characteristics*4 | | | | |
| | Aging Temperature | Gelation Start Temperature | Temperature*2 or Pre-gelation Temperature*3 | Mold Pin Temperature | | Gelation strength while being formed | Film Elasticity | Disintegration time (min) | |
| | (° C.) | (° C.) | (° C.) | (° C.) | Transparency | | | pH 1.2 | pH 6.8 |
| Example 10 | 26.0 | 54.0 | 74.0 | 82 | ◎ | ○ | ○ | >120 | 4.15 |
| Example 11 | 26.0 | 58.0 | 75.0 | 85 | ◎ | ○ | ○ | >120 | 3.84 |
| Example 12 | 25.0 | 45.0 | 60.0 | 78 | ◎ | ◎ | ◎ | >120 | 4.46 |
| Example 13 | 28.0 | 50.0 | 60.0 | 85 | — | ◎ | ◎ | >120 | 2.56 |
| Example 14 | 27.0 | 51.0 | 60.0 | 80 | ○ | ◎ | ○ | >120 | 4.51 |
| Example 15 | 28.0 | 49.0 | 60.0 | 82 | ○ | ○ | ◎ | >120 | 4.35 |
| Comparative Example 2 | 26.0 | 48.0 | 47.0 | 80 | ◎ | △ | △ | >120 | 4.12 |

*1In Examples 3-15, capsules were prepared using a hot-pin process, which is a kind of thermal gelation.
*2The aqueous compositions of Examples 3-15 were heated to a gelation temperature.
*3The aqueous composition of Comparative Example 2 was heated to a pre-gelation temperature.
*4Characteristics of the capsules were evaluated according to the following methods, and a disintegration test was performed according to the Korean Pharmacopoeia IX (9$^{th}$ ed.).

<Transparency of Capsules>

While each dried-out capsule was held against a fluorescent light, turbidity of the capsule was graded by visual inspection into one of three following categories.

◎: clear

○: slightly unclear (if capsule surface appears slightly rough or if undissolved impurities are seen)

△: hazy

<Gelation Strength while being Formed>

The gelation strength of each capsule was graded to one of three categories below, by measuring the time (t=t) when the coated aqueous composition started to flow down from the time (t=0) when the mold pin coated with the aqueous composition was removed from the aqueous composition and placed at room temperature (t=0).

◎: The aqueous composition did not flow for 60 seconds or longer.

○: The aqueous composition started to flow between 30 to 60 seconds.

△: The aqueous composition started to flow within less than 30 seconds.

<Elasticity>

Ten dried-out capsules from each example were strongly pressed 5 times with the hand (25° C., 60% RH), and then the number of cracked capsules was counted to grade the elasticity of capsules of each example into one of three following categories.

◎: Zero to two capsules were cracked

○: Three to five capsules were cracked

△: More than five capsules were cracked

Referring to Table 3, the capsules prepared according to Examples 1-15 did not disintegrate for at least 2 hours in gastric juice conditions, but disintegrated within 5 minutes in the small intestinal juice condition. This indicates that the capsules of Examples 1-15 have enteric characteristics. In addition, the capsules of Examples 1-15 appear to have good characteristics in terms of transparency, gelation strength, and film elasticity. However, although having good transparency, the capsules of Comparative Example 2 appear to be poor in gelation strength and in film elasticity.

While the present invention has been particularly shown and described with reference to the attached drawings and exemplary embodiments thereof, it will be understood by those of ordinary skill in the art that various changes in form and details may be made therein without departing from the scope of the present invention as defined by the following claims.

The invention claimed is:

1. A method of preparing an enteric hard capsule, the method comprising:
    dissolving an enteric base material, a capsule forming aid, and a neutralizing agent in water at room temperature to prepare an aqueous composition;
heating the aqueous composition to a first temperature that is higher than a gelation start temperature of the aqueous composition by about 1° C. to about 20° C.;
    cooling the heated aqueous composition to a second temperature that is lower than the gelation start temperature by about 15° C. to about 40° C.;
    immersing a mold pin heated to a third temperature that is higher than the gelation start temperature into the aqueous composition by about 10° C. to about 40° C.;
    removing the mold pin from the aqueous composition to obtain a film coated on the mold pin;
    maintaining the film on the mold pin at a fourth temperature that is higher than the gelation start temperature for a first time period to fix the film onto the mold pin, wherein the fourth temperature is from about 60° C. to about 80° C., and the first time period is from about 1 minute to about 15 minutes; and
    drying the fixed film at a fifth temperature for a second time period to obtain a capsule shell, wherein the fifth temperature is from about 20° C. to about 40° C., and the second time period is from about 30 minutes to about 60 minutes,
    wherein the enteric base material comprises at least one compound selected from the group consisting of hydroxypropyl methyl cellulose phthalate (HPMCP) and hydroxypropyl methyl cellulose acetate succinate (HPMCAS),
    wherein the capsule forming aid comprises at least one compound selected from the group consisting of hydroxypropyl methylcellulose (HPMC) and methylcellulose (MC), wherein the neutralizing a agent comprises an alkaline material.

2. The method of claim 1, wherein an amount of the enteric base material is from about 8% to about 25% based on the total weight of the aqueous composition.

3. The method of claim 1, wherein an amount of the capsule forming aid is from about 1% to about 12% based on the total weight of the aqueous composition.

4. The method of claim 1, wherein an amount of the neutralizing agent is from about 0.5% to about 5% based on the total weight of the aqueous composition.

5. The method of claim 1, wherein the preparing of the aqueous composition further comprises adding about 0.01% to about 1.0% of an emulsifier based on the total weight of the aqueous composition, to water.

6. The method of claim 1, wherein the preparing of the aqueous composition further comprises adding about 0.1% to about 4.0% of a plasticizer based on the total weight of the aqueous composition, to water.

* * * * *